(12) United States Patent
McKlarney

(10) Patent No.: US 8,887,328 B2
(45) Date of Patent: Nov. 18, 2014

(54) SYSTEM FOR COOLING A BODY USEFUL FOR REDUCING THE EFFECT OF HOT FLASHES

(76) Inventor: Christopher McKlarney, Peterstown, WV (US)

(*) Notice: Subject to any disclaimer, the term of this patent is extended or adjusted under 35 U.S.C. 154(b) by 315 days.

(21) Appl. No.: 13/208,178

(22) Filed: Aug. 11, 2011

(65) Prior Publication Data

US 2013/0036549 A1  Feb. 14, 2013

(51) Int. Cl.
| | | |
|---|---|---|
| *A47G 9/08* | (2006.01) | |
| *A61M 19/00* | (2006.01) | |
| *A47G 9/02* | (2006.01) | |
| *A47C 21/04* | (2006.01) | |
| *A61F 7/00* | (2006.01) | |
| *A61F 7/02* | (2006.01) | |

(52) U.S. Cl.
CPC .............. *A47C 21/044* (2013.01); *A47G 9/08* (2013.01); *A61F 2007/0094* (2013.01); *A61F 2007/0067* (2013.01); *A61M 19/00* (2013.01); *A61J 2200/44* (2013.01); *A61F 2007/0001* (2013.01); *A47G 9/0215* (2013.01); *A61F 2007/0257* (2013.01); *A61F 2007/0093* (2013.01)
USPC ................. 5/413 R; 5/421; 5/423; 62/259.3

(58) Field of Classification Search
USPC ........... 5/413 R, 413 AM, 421, 423; 607/104, 607/108; 2/2, 2.1, 7
See application file for complete search history.

(56) References Cited

U.S. PATENT DOCUMENTS

| | | | |
|---|---|---|---|
| 4,146,933 A | 4/1979 | Jenkins et al. | |
| 4,691,762 A | 9/1987 | Elkins et al. | |
| 5,383,918 A | 1/1995 | Panetta | |
| 5,473,783 A | 12/1995 | Allen | |
| 5,956,963 A | 9/1999 | Lerner | |
| 5,991,666 A | 11/1999 | Vought | |
| 6,354,099 B1* | 3/2002 | Bieberich | ............ 62/259.3 |
| 7,100,394 B2 | 9/2006 | Bieberich et al. | |
| 7,716,940 B2 | 5/2010 | Farnworth et al. | |
| 7,721,349 B1 | 5/2010 | Strauss | |

(Continued)

FOREIGN PATENT DOCUMENTS

WO  WO2010009360  8/2010

*Primary Examiner* — Peter M Cuomo
*Assistant Examiner* — Brittany Wilson
(74) *Attorney, Agent, or Firm* — New River Valley IP Law, PC; Michele L. Mayberry (57) ABSTRACT

The present invention relates to systems, methods, and devices for treating the effects of menopause. More specifically, embodiments of the present invention relate to systems, methods, and devices used while sleeping for automatically detecting an imminent hot flash and for preventing and/or controlling the symptoms associated with hot flashes, such as an elevated body temperature, sweating and/or chills so that the person using the system remains sleeping and is not disturbed by the hot flash onset. Preferred embodiments include an automated body cooling system comprising: an elongated cloth bag comprising a lower open-ended chamber for enveloping a person's body and an upper closed chamber for receiving a flow of air from a fan; a fan operably connected with the upper chamber of the bag to provide a stream of air into the bag for over inflating the bag to provide positive pressure; a sensor for detecting at least one of relative humidity, skin temperature, or sternal skin conductance information; and a control module in operable communication with the sensor for receiving and processing the information from the sensor and for turning the fan on and off in response to the information received being above or below a desired set point.

15 Claims, 2 Drawing Sheets

(56) References Cited

U.S. PATENT DOCUMENTS

| | | |
|---|---|---|
| 2005/0251913 A1 | 11/2005 | Mccall et al. |
| 2010/0204764 A1 | 8/2010 | Garetz |
| 2013/0031722 A1* | 2/2013 | Wong .............................. 5/423 |

* cited by examiner

SYSTEM FOR COOLING A BODY USEFUL FOR REDUCING THE EFFECT OF HOT FLASHES

BACKGROUND OF THE INVENTION

1. Field of the Invention

The present invention relates to systems, methods, and devices for treating the effects of menopause. Embodiments of the present invention relate to systems, methods, and devices used while sleeping for automatically detecting an imminent hot flash and for preventing and/or controlling the symptoms associated with hot flashes, such as an elevated body temperature, sweating, and/or chills so that the person using the system remains sleeping and is not disturbed by the hot flash onset.

2. Description of Related Art

Vasomotor symptoms, including hot flashes and night sweats, are the most frequently reported symptoms of menopause. As many as three out of four women experience hot flashes during menopause, according to the Mayo Clinic. Hot flashes—as defined by The National Institute of Health (NIH)—are a sudden temporary onset of body warmth, flushing, and sweating.

Sufferers of menopausal hot flashes have experienced numerous, bothersome symptoms, including a feeling of mild warmth to intense heat spreading through the upper body and face; perspiration, mostly on the upper body; and a chilled feeling as the hot flash subsides. In response to a hot flash, a woman's heart rate and skin blood flow increase, but the internal body temperature may drop by as much as three or four degrees as the body struggles to correct the imbalance. Hot flashes, which typically subside within a couple of minutes, can sometimes last as long as thirty minutes. Especially bothersome, is that nighttime hot flashes (night sweats) can wake a person up from a sound sleep, or even bother a sleeping partner.

Hormone replacement therapy can provide relief for some sufferers of menopause and may help to reduce hot flash intensity and/or frequency. Changes in diet have also been recommended, in particular, to include more soy-based products in the diet. Lifestyle changes and chemical therapeutics, however, are not viable alternatives for some women.

There exist numerous ways of cooling a body. For example, U.S. Pat. No. 4,146,933, incorporated by reference herein in its entirety, describes a conditioned-air suit to be worn over a user's entire body, including the head, which has several hose connections for delivering cool air as needed in response to certain environmental conditions. Such suits are restrictive and cumbersome and do not allow for a user to switch easily from being in the protected environment to an unprotected situation.

U.S. Pat. No. 5,383,918, incorporated by reference herein in its entirety, provides another type of cooling suit for a patient undergoing a medical procedure or for a patient with hypo- or hyperthermia. This suit is intended to be worn over the entire body, including the head, and suffers from the same disadvantages as just described.

A surgical drape is provided by U.S. Pat. No. 5,991,666, which is incorporated by reference herein in its entirety. The drape, similar to a dense blanket, can be configured to circulate a coolant through the drape and when contacting a patient's body will cause cooling to the body through conduction. A person using such a drape during sleep would find it restrictive and not soft and comfortable as compared to sheets and blankets that the user may have become accustomed to using. The drape also fails to provide a mechanism for wicking moisture away from the body, which may occur from hot flashes manifested as night sweats.

A fan-free blanket has also been proposed by U.S. Pat. No. 7,721,349, which is incorporated by reference herein in its entirety. The blanket comprises a water-absorbent side and a waterproof side. The blanket is positioned over a user with the waterproof side facing the person. With the water-absorbent side facing up and away from the body, a cool glass of water is poured onto the blanket. The body is then cooled by conduction and by the water evaporating into the air around the person to cool the air on the outside of the blanket. Such devices do not allow for the user to remain sleeping due to the user having to get up out of bed to obtain cold water and then pour the water on the blanket. This method also focuses on cooling air above the blanket rather than below where the user needs it most.

Even further, US Published Patent Application No. 2005/0251913, incorporated by reference herein in its entirety and entitled "Portable Padded Air Flow Pouch," provides another blanket-type solution to keeping a body cool. Exemplified in the published application is an air flow pouch for containing perforated tubing which comprises a net-type cloth material front to allow air to escape and an air resistant interior back to reflect air through the front of the pouch. Proposed uses of the pouch include storing the pouch under a pillow until menopausal symptoms arise, then positioning the pouch over the user's body, and turning the device on to allow air to flow out of the pouch and be distributed over the user's body.

A convective cooling type drape is provided by U.S. Pat. No. 6,354,099, which is incorporated by reference herein in its entirety. Instead of tubing inserted into the material of the drape to provide a structure for containing and/or directing the cool air, the drape is formed of multiple chambers for holding the circulating air. One side of the chamber includes multiple exhaust holes through which air is allowed to escape from the chamber and exit toward the person. The drape has additional openings between the chambers to allow for evaporative cooling of the person's body.

International Patent Application Publication No. WO/2010/093604, incorporated by reference herein in its entirety and entitled, "Method for Treating Hot Flashes Associated with Menopause During Sleep," describes a method and device for automatically detecting the onset of a hot flash while the subject is sleeping, and of cooling the subject using a cold fluid circulating through a vest or a mattress pad, before sweating and/or chills develop and awaken the subject. A temperature sensor is attached to the subject's skin, and is connected to a computer or microprocessor. The subject wears a vest that is connected to a coolant circulation system. Alternatively, the subject lies on a mattress pad that is connected to a coolant circulation system. During the night, if the subject's skin temperature is raised more than a predetermined amount within a specified time period, or rises above a predetermined threshold temperature, the coolant circulation system is activated for a fixed period of time. The cooled vest or pad helps to draw heat away from the subject's skin reduces the symptoms of hot flash.

The most common complaint of women suffering from night-time hot flashes is that the sufferer is woken up by the sudden body change. A major disadvantage of the existing body cooling technology is that the user still must wake up before applying the advantages of the body cooling systems, which does not solve this problem. If the systems were already activated while the person was sleeping, the person may become too cool for comfort.

What is needed is a system capable of providing comfort to a user during sleep and which is automatically activated to provide relief to the user without disturbing or requiring the user to wake before the system begins working.

SUMMARY OF THE INVENTION

Systems of the invention can be used to provide relief for hot flashes experienced by a body, especially in response to menopause symptoms. Embodiments of the invention can also be used to decrease a person's body, blood, or skin temperature which may be elevated due to sickness, infection, or injury.

Embodiments of the invention provide automated systems for cooling a body, as well as methods of using the automated systems, which comprise: a fan; a sensor for detecting a person's body temperature, skin temperature, skin conductance, and/or relative humidity; a control module in operable communication with the sensor for receiving data from the sensor and in operable communication with the fan for turning the fan on or off in response to receiving data with a value above or below a set point.

A wireless cooling system according to embodiments of the invention includes three separate pieces of hardware: fan module, desktop control module, and watch or chest module. Although a wireless configuration is preferred, the components of the system can also be interconnected with wires. The three pieces work together to intelligently and accurately detect increases in the user's skin temperature or other physiological condition and power on a cooling fan when necessary.

Preferred systems comprise: a fan; a sensor for detecting sternal skin conductance and relative humidity; a control module in operable communication with the sensor and the fan for receiving data from the sensor and for turning the fan on or off when the data is above or below a desired set point.

Systems of the present invention include automated systems for controlling a fan in response to a change in one or more physiological conditions. The fan in systems of the invention can be controlled by turning the fan on or off or by changing the speed of the fan. Preferred systems of the invention monitor physiological condition(s) that are susceptible to change in response to the onset of menopause symptoms, yet any physical condition can be monitored and used for the set points.

Specific embodiments include an automated system for cooling a body comprising: (a) a bag capable of encompassing all or part of a person's body comprising an absorbent and porous material for reducing moisture and heat in the bag; (b) a fan operably connected with the bag to provide a stream of air into the bag; (c) a sensor for detecting a person's skin temperature and/or sternal skin conductance, in operable communication with a control for the fan, for activating or deactivating the fan or increasing or decreasing fan speed in response to detecting a selected skin temperature and/or sternal skin conductance has been reached.

A preferred embodiment according to the invention is an automated body cooling system comprising: an elongated cloth bag comprising a lower chamber for enveloping a person's body and an upper chamber for receiving a flow of air from a fan; a fan operably connected with the upper chamber of the bag to provide a stream of air into the bag; a sensor for detecting a physiological condition, such as sternal skin conductance; and a control module in operable communication with the sensor for receiving and processing the physiological information from the sensor and for turning the fan on and off in response to the information received.

Other automated systems for cooling a body can comprise: (i) a sleeping bag made of (a) two fabric sheets joined to form a bag for receiving and covering the body of a user, and (b) an air-resistant sheet of material joined to one of the fabric sheets in a manner to form an upper closed chamber; (ii) a duct in operable communication with the upper closed chamber; (iii) a fan in operable communication with the duct having a speed of 200-400 CFM for inflating the closed chamber and creating a positive airflow from the closed chamber through the fabric sheet into the bag; (iv) a sensor module with one or more sensors for obtaining at least one of a skin temperature, skin relative humidity, or sternal skin conductance measurement; and (v) a control module in operable communication with the sensors for receiving the measurement, comparing the measurement to a set point, and turning the fan on or off in response to the measurement respectively exceeding or falling below the set point.

Embodiments of the invention can comprise a sleeping bag, wherein the fabric sheets joined to form the bag comprise an absorbent and porous material for reducing moisture and heat in the bag.

Additionally, the sensor module can comprise any number of sensors for monitoring any number of physiological or environmental conditions. In preferred embodiments, the systems comprise a sensor module with a skin temperature sensor and a sternal skin conductance sensor. In other preferred embodiments, the sensor module can comprise skin temperature, skin relative humidity, and sternal skin conductance sensors. Further, a single physiological condition can be monitored and/or measured, such as by using a sensor module with a skin relative humidity sensor.

In embodiments, the control module is programmed to activate the fan in response to skin temperature and skin conductance being above a set threshold that is below an amount indicative of a hot flash, such that the cooling system is activated prior to the onset of a hot flash. The control module can be further programmed to de-activate the fan in response to skin temperature and skin conductance being below a set threshold. The sensor and control module can be hard wired or can communicate wirelessly. A fan module can be independently included in the systems of the invention or can be incorporated as part of the control module. Embodiments can further comprise a fan module for receiving instructions from the control module for turning on and off the fan. In such embodiments, the fan module and control module can be hard wired together or can communicate wirelessly to operate the fan unit.

Any physiological condition or combination of conditions can be monitored and used to trigger activation of the fan. For example, it may be desired that the fan be activated upon three or more changes in physiological conditions exceeding a set threshold. Indeed, any number of physiological conditions can be measured and used in the processing means of the control module to determine whether the fan should be activated, slowed down, or increased in speed.

Specific preferred embodiments are described in more detail below.

BRIEF DESCRIPTION OF THE DRAWINGS

These drawings illustrate certain aspects of some of the embodiments of the present invention, and should not be used to limit the invention.

DETAILED DESCRIPTION OF PREFERRED EMBODIMENTS

One of the objects of the present invention is to provide a system for reducing or preventing the onset of hot flash symptoms and/or night sweats. What is needed is a system capable of providing comfort to a user during sleep and which is automatically activated to provide relief to the user without disturbing or requiring the user to wake to activate the system or wake before the system begins working.

Basic systems according to embodiments of the invention can comprise a fan, a control module, and a sensor. These elements make it possible for a person to mitigate the effects on their body of changes in certain physiological conditions that may occur during sleep without having to wake up to make physical adjustments to their environment, such as removing or adding covers or turning on or off a fan. Systems according to the invention can comprise one or more of these elements, or additional features described in this specification, or any combination thereof.

Although especially preferred embodiments may comprise most of the individual features described in this specification, it is important to note that other combinations of more or less features are also encompassed by the invention. Methods of cooling a body are also within the scope of the invention and include any method of using any of the systems described in this specification.

Especially preferred embodiments of the invention include: an elongated cloth bag or sleeping sack comprising a lower, open-ended chamber for enveloping a person's body and an upper closed chamber for receiving a flow of air from a fan; a fan operably connected with the upper chamber of the bag to provide airflow into the upper chamber and over inflate the chamber; a sensor for detecting sternal skin conductance and/or relative humidity information; and a control module in operable communication with the sensor for receiving and processing the information from the sensor and for turning the fan on and off in response to receiving sensor information above or below a set point or measurement values that have deviated from the normal values for a user.

I. Control System for Activating the Body Cooling System

Preferred embodiments of the invention include a wireless cooling system with three separate pieces of hardware: a fan module, a desktop control module, and watch or chest module. An overview of this hardware is provided below.

The fan module can be attached physically and electrically to the cooling fan and primarily performs two tasks. First, the fan module contains the AC/DC conversion circuitry, and thus is the only device of the system that plugs into a standard 120V, 60 Hz wall outlet. This unit converts the high voltage AC power signal to a lower-level DC voltage used for the digital electronics. This module not only powers its own circuitry, but also powers the desktop module/control module. The second task that this fan module accomplishes is powering on and off the cooling fan as per a digital signal from the desktop control module. It is not critical to the invention that a fan module and control module are independent or distinct and both can be combined in a single unit.

The fan attached to this module can be swapped for other fans easily, as the system contains circuitry capable of handling the current requirements of nearly any fan that could be used on the scale of human cooling. In embodiments, the systems can have an electrical current limit of 30 amps at 120V, which is nearly 6 times the maximum current consumption of the turbine fan currently in use (5.4 amps).

The desktop module can plug into the fan module by way of a standard RS232 cable. These cables will be included with the system, but can be obtained at any electronics store (i.e. RadioShack) or even most grocery stores. By way of the RS232 cable, the desktop module is powered from the fan module. Alternatively, the desktop module can have an independent source of power by plugging the desktop module into a standard outlet. The desktop module possesses two responsibilities. First, the desktop module receives wireless signals from the watch module or other sensor as to power on or off the cooling fan. This on/off signal can be transmitted to the fan module using the RS232 cable or by a wireless signal. The second purpose of the desktop module is charging the battery of the sensor. This is accomplished using a 6" barrel-connector cable coming out of the control module.

LED's disposed in the desktop module can be used to display the power status of the module, as well as the charging and battery status of the watch module. For example, a green LED and orange LED can be used to indicate the desktop module's power status as well as the battery status of the watch module. The green LED can turn on when the desktop module is plugged into a powered-on fan module. This LED indicates not only the power status of the fan module, but also indicates that the onboard battery charger circuit is prepared for action.

When the sensor module (e.g., wrist or sternum sensor) is plugged into the desktop module, two LED statuses are possible. First, a green LED can be illuminated to indicate the battery of the sensor module is charged. The orange LED can be lit to indicate the battery is charging. Upon completion of charge, the orange light will turn off and the green light will once again turn on. Again, if the watch module is not plugged in, the green light will be on, used simply as a power indicator.

A green LED nearest the power switch indicates the digital power and RF connectivity of the module. Upon flipping the switch to the ON position (towards the green LED), a short delay will be followed by this LED turning on. This indicates that the radio and digital electronics were powered up and a wireless network was initialized, all occurring during this short delay. Once the light is on, all electronics are operating as programmed, and the RF link has been successfully initialized.

The final piece of the wireless cooling system is the mobile watch module, or sensor module for detecting physiological changes in the user. This module is the brain of the system, making all temperature readings (or other sensor readings), decisions and transmissions. In embodiments, the temperature module can possess a temperature resolution of 0.03° C. (0.05° F.).

The watch module is preferably controlled by a Microchip Technology PIC18LF4620 digital microcontroller. Using a 2.4 GHz wireless module using Microchip's MiWi (simpler version of the common Zigbee protocol) wireless communication protocol, using the standard IEEE 802.15.4, data is transmitted to and from the desktop module to power the fan on or off. The microcontroller also powers the transmitter and various other electronics on and off as needed to save battery power. Additionally, the microcontroller itself sleeps in a low-current mode and only wakes every two seconds to take readings or detect if the user has flipped any switches. The LED on top of the module indicates battery, RF and power status.

The watch module can attach to any normal sweat band for comfort and simplicity in cleaning, as the system is attached completely by industrial strength Velcro. A small cut in the wrist band can be made to insert the temperature sensor to the inside of the wrist band if the module switches are to be worn in a secure wrist position (facing the hand or forearm). This orientation eliminates the possibility of inadvertent flipping of the switches by rubbing sheets or other objects. Optimal operation of the sensor will result from this sensor being as far as possible from the edge of the wrist band and centered under the watch module.

The temperature sensor can be a Texas Instruments TMP37. The TMP37's high sensitivity of 0.02 Volts/° C. allows for the system's high resolution temperature readings. The sensor is sealed in clear high-strength super glue. This glue is safe for skin use, as surgical glue is of nearly identical formulation, differing only in ingredients that make the glue flexible. Use of this sensor and sealant was based on market availability, cost, resolution and ease of use. Other sensors can also be used.

Powering the watch module is a 3.6V lithium-ion rechargeable battery. This battery is capable of powering the module for one to two weeks (assuming 8-hour nights) of normal operation before needing a charge (depending on transmissions, switches being used, etc). Additionally, included in the battery is a safety circuit that protects the battery from overheating or explosion in the case of an inadvertent short circuit. Additionally, this circuit prevents over or under-charging of the battery. When the battery is detected as low, a short LED flash will occur every two seconds. When this occurs the battery should be recharged.

The watch module is equipped with two slide switches, one being the power switch and the other a power override switch. Sliding the power switch to the right powers the watch module on, beginning the RF linking and temperature detection stages of the device's programming. Sliding this switch back to the left powers the module off and puts the battery in charge mode. In this mode, the module can be plugged into the desktop module for charging.

The second switch is a power override switch. With the switch to the left, the module will operate as normal, sensing temperature and turning on the fan at the appropriate set points. By sliding the switch to the right, the detection system is manually overridden, and the fan will turn on "immediately". "Immediately" is relative in this context as to save power, the system only checks this switch every two seconds. Therefore, upon manually overriding the system using this switch, up to a two-second delay may be experienced before the fan actually powers on or powers back off.

The wireless cooling system is controlled by the PIC18LF4620 microcontroller contained within the watch module. All sensing, decisions and wireless transmissions come from this module and the underlying algorithm controlling it.

Following a power-up of the desktop module, the user will power on the watch module. The watch module will establish a wireless connection to the desktop module and blink the LED twice to inform the user that the connection has been established. Now, the watch module will ensure that the skin temperature is stable and ready to accurately detect fluctuations in real time. The system waits for the sensed skin temperature to stabilize to within a 0.15° C. envelope for 60 seconds. In other terms, the module waits until the temperature of the skin remains within 0.15° C. of itself for a minimum of 60 seconds. The time that is needed to ensure this condition varies depending on temperature, environment, and amount of time that the watch module has been in place on the user's wrist. Upon meeting this condition, the green LED will blink four times: one long flash followed by three short flashes. The system is now live and detecting in real time.

During normal real-time operation, the system is looking for an increase in temperature relative to a baseline temperature. In embodiments, this temperature increase is set to 1.11° C. (2.00° F.). This change in temperature relative to the baseline, $T_{on}$, which is set and reset to the temperature of the skin 60 seconds previous to the current temperature reading. This threshold must be crossed definitively and consistently for 10 seconds. At that time, the watch module sends a command to the desktop module (and then to the fan module) to power on the cooling fan. The purpose of comparing the current skin temperature to the skin temperature 60 seconds in the past is to increase the reliability and robustness of the system.

During a normal night's sleep, environmental temperature changes, moving under and out of covers, and normal body temperature fluctuations will occur. By comparing the current temperature to the temperature 60 seconds in the past allows for the baseline to continuously adjust with the small, slow fluctuations while still allowing for the detection of the sudden onset of skin temperature flashes. This ensures that if the temperature rises by at least $T_{on}$ within a time period of 60 seconds, a positive detection is made. All other fluctuations are ignored.

Additionally, to ensure that the fan is not powering on, powering off, and repeating continuously due to small fluctuations in the temperature near $T_{on}$ once a detection is made, a digital Schmitt trigger has been programmed for operation. This algorithm turns the fan on at $T_{ON}$, and waits for the temperature to drop to a threshold temperature $T_{OFF}$, that is closer to a saved baseline temperature before powering off the fan. The saved baseline temperature to which these readings are compared is the skin baseline temperature that was present 60 seconds before the spike is detected. This point of reference ensures that the fan is powered on until a comfortable skin temperature is again established, and then powered off. In version 1.0, $T_{ON}$ is set to 1.11° C. (2.00° F.) and $T_{OFF}$ is set to 0.25° C. (0.45° F.).

After the fan has been powered off from a positive temperature spike detection, a temperature stabilization delay is executed, exactly the same as at system power-up, followed by the normal four-flash LED indication of completion. At that point, the module has established that the skin temperature is again stable and at a comfortable temperature, and begins detecting, once again, in real time.

The watch module is equipped with a fan power override switch. In one position, the fan override is off and the module operates normally. When the switch is engaged to the right, the detection algorithm is overridden and the fan is manually powered on regardless of any other real time operations of the system. It is important to note that a delay of about 2 seconds may be experienced between engaging the switch and the fan powering on. This is normal and is a result of the microcontroller needing to wake up and recognize the change in the switch status. To power the fan off, simply slide the switch back to the left. The same delay will be seen while powering off in this manner. It is important to note that this feature can be used during real time operation if the fan is on. If the fan is powered on due to a temperature spike and the user sees fit to have the fan power down early, sliding the override switch to the on position, leaving it in there for several seconds (to allow the microcontroller to wake up and recognize the status), then sliding the switch again to the off position will power down the fan. If this situation occurs, it is important to understand that normal operation will not continue until normal conditions are met. This entails the skin temperature to drop below the preset $T_{OFF}$, followed by a stability delay (followed by four pulse LED flash).

In embodiments, various types of sensors can be used. For example, a temperature sensor comprising a simple 8-pin SOIC chip was installed and sealed for the use against the skin. Other more elegant temperature sensors are also available, such as that from Measurement Specialties. In particular, the 409A and 427 series temperature sensors may be desired for some situations, especially where durability and/or sensitivity of the system are a concern or where it is desired to eliminate several electrical components from the system in order to improve size, cost and power use. The sensors of interest are ruggedized, washable, and smaller than the current sensor.

Skin conductivity measurement circuitry can be used in addition or as an alternative to temperature measurement. Likewise, relative humidity measurements can also be used alone or in combination with other parameters mentioned herein. Skin relative humidity is a factor of skin temperature and sweat rate. Relative humidity of the air at the skin surface can also be used. Cooling systems of the invention can be activated when a sensor detects a change in skin relative humidity or when the skin relative humidity reaches 100%, which indicates a wet skin condition, or when a change in skin relative humidity is experienced below this level prior to the onset of symptoms.

Several factors that can affect performance of such a system should be taken into consideration in designing cooling systems using such sensors and circuitry. Most notably, skin conditions including temperature, humidity, electrolyte presence, etc can significantly affect conductivity (changes in millions of ohms). An adaptive algorithm should be used to compensate for these effects. Also placing probes near a watch, chest strap, or sweat band may alter the accuracy of the conductivity readings. This is due to the principle that conductivity in thermal flashes drops as a result of perspiration output. As a result of wearing anything over the skin, perspiration will result, and proximity of skin probes near this perspiration may produce false positive conductivity readings. Real time testing of probe placement will help in solving this problem.

Another variation can be to eliminate the 2.4 GHz wireless module responsible for wireless communication in the system. The printed antenna, as well as circuitry can quickly and easily be incorporated into the main printed circuit board with the other electronics. This will reduce cost and size significantly.

The wireless detection systems can also be upgraded by exchanging the onboard microcontroller from the current 8-bit PIC18 system to a 16-bit PIC24 system. Certain PIC24's possess lower power consumption, and have a broader scope of use, and are slightly less expensive than the PIC18 series.

The automated control system can include a probe or other sensor for monitoring, measuring, or detecting one or more physiological conditions in addition to or alternatively to skin temperature. The sensor is preferably in operable communication with the user of the system to collect the pertinent data. The sensor is configured to transmit the collected data to a control module for operating a fan or other cooling apparatus. The control module processes the data received to determine whether to activate or de-activate the fan.

Any physiological condition can be measured, including skin temperature, body temperature, heart rate, relative humidity, or skin conductance. Any single physiological condition or combination of conditions can be used to trigger activation of the cooling system. For example, the control module can be configured to activate the fan when a person's skin temperature has elevated by 1 degree, or when a change in skin conductance of 2 microsiemens or more has been detected, or when a change in heart rate and/or a detectable increase in relative humidity has been detected.

In embodiments, sensors used in embodiments of the invention can be configured to detect changes in sweat gland activity of the user and/or changes in sternal skin conductance. Such sensing devices can be used in addition to or alternatively to the temperature sensors. One such sensor can be operably configured to monitor and detect changes in skin conductance of the user. Skin conductance, also known as galvanic skin response (GSR), electrodermal response (EDR), psychogalvanic reflex (PGR), skin conductance response (SCR) or skin conductance level (SCL), is a method of measuring the electrical conductance of the skin, which varies with its moisture level. This is of interest because the sweat glands are controlled by the sympathetic and parasympathetic nervous systems, so skin conductance is used as an indication of psychological or physiological arousal. Research shows that skin conductance may change during a hot flash or night sweats.

Skin conductance monitors measure the electrical conductance (which is the inverse of the electrical resistance) between 2 points, and are essentially a type of ohmmeter. The two paths for current are along the surface of the skin and through the body. Active measuring involves sending a small amount of current through the body. More specifically, there are only a couple of places where it is widely recognized as easy and reliable to measure the skin conductance response: the palms and the soles of the feet. In these places there is a high density of the eccrine sweat glands. The primary function of eccrine glands is thermoregulation—evaporative cooling of the body. In either of these areas, the conductance is measured by placing two electrodes next to the skin and passing a tiny electric charge between the two points. When the subject increases in arousal, his/her skin immediately becomes a slightly better conductor of electricity. This response can then be measured and communicated.

When the body is significantly overheated and there is a lot of perspiration, the overall level of skin conductance will indeed climb. Skin conductance, however, is not simply temperature-based. A high conductance can be exhibited when the hands are cold (e.g., when nervous) and a low conductance can be exhibited when the hands are warm (e.g., such as when very relaxed). Thus, if using skin conductance as a trigger for activating the body cooling system according to the invention, a baseline should be set for the sensor for each particular user, such as the skin conductance of the user in bed at rest just prior to going to sleep. Normal readings, for skin conductance, in a relaxed state are around 2 µS, but readings can vary greatly with environmental factors and skin type. Due to the response of the skin and muscle tissue to external and internal stimuli, the conductance can vary by several microsiemens. When correctly calibrated, the skin conductance can measure these subtle differences.

Sensors for measuring and/or detecting skin conductance can be configured for example to operate using a 6V battery as a power source and to deliver an average current ranging from about 10-60 microamps, considering an average skin resistance from about 0.1-0.4 megaohms. Representative skin conductance sensors compatible with the systems and methods of the invention include the Skin Conductance Flex/Pro Sensor SA9309M, which has the following characteristics:

TABLE I

| Specifications for Skin Conductance Flex/Pro Sensor SA9309M | |
| --- | --- |
| size | 3.5 cm (1.4") |
| weight | 25 g (1 oz) |
| signal input range | 0-30.0 µS |
| accuracy | ±5% and ±0.2 µS |

For example, in practice the sensor may be worn on the user's wrist or on the user's chest. The sensor will typically be in contact with the user's skin and wirelessly in communication with the control module. The sensor can be calibrated to the person's average physiological conditions by monitoring these conditions of the person while resting in the bag (not during a time of experiencing hot flashes) over a short period of time, such as 1-5 min. The fan control mechanism can then be triggered by the control module when the sensor detects a change in physiological condition that exceeds or falls below a certain set point. For example, if skin temperature is measured a change of anywhere from about 0.5°-10° F., preferably from about 1° to about 4° F. can be used to trigger activation of the cooling system. With respect to skin temperature, the sensor is preferably sensitive enough to be capable of detecting changes in skin temperature in the range of $1/10^{th}$ to ½ to 1 degree.

Thus, when the person wearing the wristband or sternal sensor experiences a hot flash and her temperature rises, the fan can be automatically turned on when the sensor detects the specified change in skin temperature. According to this method, the user of the system will not have a need to wake up or wake completely to manually control her environment. Preferably, the sensing and control system are programmed to skin temperatures typically experienced by the individual using the system and the system is turned on at a point before the highest expected skin temperature is reached during the hot flash episode so that the intensity of the hot flash can be reduced and/or avoided and the user remains in a sleep state. This same principle can be applied concerning measuring any physiological condition or combination of conditions.

Embodiments of the invention can include temperature and/or humidity sensors in the bag or under the bed sheets as well to detect changes in the sleeping environment. The fan can be activated when any of the sensors (whether located on the user's wrist or sternum to measure skin temperature or other parameters or located within the bag to measure the environment within the bag) has determined a certain temperature or humidity level has been reached. The automated system can be programmed to activate the fan when a particular combination of skin temperature, temperature within the bag, and humidity within the bag has exceeded a certain set point, such as a user's desired comfort level.

The sensor can be hardwired to the control module and the fan control mechanism, but is preferably connected wirelessly. The control system can be programmed to turn on the fan when the sensor determines a pre-set skin temperature (or other physiological or environmental condition) has been reached or when a pre-set change in skin temperature (or other physiological or environmental condition) has been reached. In embodiments, the sensor can measure body temperature, blood temperature, and/or skin temperature and be programmed to trigger activation of the fan when a specific body temperature and/or specific combination of body, skin, and/or blood temperature has been reached. When referring to cooling a body in this disclosure, it can refer to any or all of reducing a person's body, blood, or skin temperature. Additionally, although the term cooling may be used it is intended to encompass any change in physiological condition, such as a reduction of sweat. Evaporative cooling (i.e., sweating) is the primary means by which the human body controls body temperature.

Sensors can also be configured to detect changes in blood, skin, body, or atmospheric temperature using infrared and/or thermal imaging technologies. In this way, a remote sensor not attached to the user can be employed. For example, the thermal imaging or infrared imaging type sensor can be incorporated into the bag and disposed to measure temperature changes of the person and/or of the environment within the bag. Such sensors can also be remotely connected or hardwired to the fan controls and disposed at a distance from the bag and/or user of the bag to measure by infrared or thermal imaging or the like temperature changes. A convenient place for such sensors include the headboard of a bed, a night stand, a wall, or other support.

II. Body Cooling and Bag Atmosphere Cooling Fan

The fan of body cooling systems according to the invention includes any fan capable of providing quiet, directed forced air. A fan small enough to fit under a bed is preferred. Multiple fan settings are also a plus.

In embodiments, the fan is ductless and is positioned in close proximity to a user of the system. Upon the control module detecting a change in a physiological condition of the user, the fan is turned on or off or is increased or decreased in speed. The air from the fan cools the user by moving the air around the user and/or coming into contact with the user's skin to cool the skin. If the user is experiencing sweating, the moving air will cool the body by evaporating the perspiration.

It may be desired in certain embodiments to contain the airflow from the fan to increase the efficiency of the fan or to provide for fanning only of the user and not a companion in close proximity to the user. For example, it may be common for two people to share a bed, only one of which may suffer from the symptoms of menopause. In such a situation, it may be desired to have the airflow from the fan come into contact only with the user of the system rather than the bed as a whole. One way to accomplish this goal is to connect the fan with a duct and/or a sleeping bag.

In embodiments where the fan is operably connected with a sleeping bag tubing can be used to capture air from the fan face and direct it into the bag. The tubing or duct can be flexible or rigid or a combination. The tubing can be inflatable by way of air pressure passing through the tubing, which would be especially comfortable for the person in the bag in cases where the tubing extends into the bag. To accomplish this goal, the material of the duct should be impermeable to air or at least air resistant in order to contain the air within the tubing. The tubing, if a portion extends to within the bag, can be perforated or otherwise configured to allow for air to escape from multiple outlets along the side of the tubing and preferably along the length of the bag to cool the person's body in more than one location.

In embodiments, the tubing is attached to an opening in the bag near the location where the person's feet would be, however, if cooling is desired to be more intense around the person's core or head, the tubing entrance into the bag can be located near the upper portion of the bag as well or alternatively. If the sleeping bag comprises a second elongated compartment (i.e., closed upper chamber), the tubing can be operably connected with the second compartment to allow for the flow of air into the second compartment, but not directly into the first from the tubing. During use, the fan is turned on to provide airflow into the closed chamber and the chamber is caused to inflate. As air continues to enter the closed chamber, ideally it is allowed to exit only through the fabric of the lower chamber and not through the upper sheet of material that is impermeable or only semi-impermeable to air. Perforations or slits may be made in the main sleeping bag in the fabric sheet disposed between the outer fabric sheet of the lower chamber and the upper impermeable sheet material such that air can more easily flow from the first compartment into the second through the perforations rather than through the pores of the fabric itself. In such embodiments, perforations or slits will be needed only in the portion of the sleeping bag that drapes over the person during use, i.e., the intermediate fabric sheet. Perforations can be strategically placed along the length of the bag and/or along the opening edge near the person's head and neck.

To deliver air flow specifically to the head, neck, shoulders, and/or upper portion of the body, a second hose or tubing can also be included, if desired. A second fan can be used to supply air flow to the second hose, or the air flow from a single fan can be split into two hoses, if desired. The hose located near the head can deliver the air through a single outlet of the hose or can be delivered through multiple vents along the length of the tubing. Multiple variations for tubing, location of the fan, and disposition of the tubing relative to the user can be applied. In preferred embodiments, it is desired to reduce the amount of airflow that extends beyond the immediate user of the system so as not to disturb a sleeping partner in bed.

Hose or tubing that is preferred includes tubing with about a 3-4 in. diameter and is operably connected to the fan in a manner that does not impede or minimizes impedance to the flow of air exiting the fan and allows for a natural spiral of airflow into the tubing from the fan. A convergent shrouded fan connecting a larger diameter fan to the 3-4 in. diameter tubing could be used. The tubing preferably comprises a flexible material that allows for some amount of bending of the tubing to facilitate positioning the fan in a number of places relative to the bag. For example, the fan can be placed under the user's bed, while the tubing extends out from under the bed to on top of the bed where the user will be located within the bag. The hose can be made of any material suitable for air flow ducts and vents, including metal, plastic, foil, rubber, cloth, or combinations thereof. Additionally, the tubing can be reinforced with wire, preferably formed in a spiral pattern along the length of the hose to provide additional structural support to the tubing. If located in an area susceptible to contacting the user's body and especially if disposed in a manner where the person's body may roll over on the hose, the hose if preferably made of a collapsible material that will collapse if rolled on by the person to provide a more comfortable sleeping atmosphere.

US Published Patent Application Nos. 2010/0221994, 2008/0060131, and 2006/0085911, which are incorporated by reference herein in their entireties and entitled "Portable Ventilation System," disclose a bed fan that can be used in embodiments of the invention. These bed fans have an integral duct in communication with the fan to transport the airflow from the fan face to the person sleeping and are configured for delivering an airflow directly to the area between the bed sheets at the foot of the bed. In embodiments, the sleeping bag can be made to envelope a duct that is integral with a fan so as to reduce the need for additional ductwork.

Generally speaking, the fan can be any device for producing airflow. Especially preferred are fans that have a quiet operation and are compact. Ideally, the fan is disposed under the person's bed and should not produce excessive noise or vibration that might disturb the sleep of the individual.

Representative fans that can be used in the systems of the invention include the Turbo-Aire brand fan by seabreeze, which provides 12-inch blades within an enclosed curved housing to deliver over 11,000 cubic feet of air per minute at a distance of 20 feet. For larger fans used in combination with smaller diameter duct work transition tubing can be used, for example, to transition between an 8-in fan face and a 4-in. duct. Another option is the Eclipse Fan, an in-line centrifugal duct fan that delivers 487 or 630 CFM. The AeroTec wall-mount, compact dock fan can also be incorporated into systems of the invention, and provides a ⅓ horsepower motor and up to 850 CFM. Other acceptable fans include the Lasko 4903 with three fan speeds and an 8-in fan diameter, which will move 190 CFM on low, 260 CFM on medium, and 310 CFM on high. A preferred fan is made by B-Air CP-1 Cub, which provides a ¼ HP motor at 115V and about 350 CFM.

Fans of the systems of the invention preferably are quiet and have a noise level of less than 60 decibels, for example from about 50-60 decibels. Generally, the higher the airflow output of the fan, the louder the fan will be. Fans with a noise output in the range of 70-78 decibels can also be used, however, sound insulation of the fan body may be highly desired to ensure the user of the cooling system does not wake.

III. Body Cooling Bag or Sleeping Bag

The sleeping bag is preferably of a sufficient size and shape to accommodate an adult female body (approximately 80 inches by 38 inches should suffice on average). In preferred embodiments, the bag is similar to a sleeping bag and may have an opening or openings on one or two sides of the bag. The opening can be closed by way of a drawstring, zipper, hook-and-loop (Velcro), or snap-type closing, for example, to allow easy and quick access to the interior of the bag. In embodiments, an opening is at the top of the bag (close to the person's head and neck) and has a drawstring closure.

The material for the bag is preferably lightweight, for example, the weight of a bed sheet or lighter. The material is also capable of absorbing moisture from the body and from humid air surrounding the body within the bag. For example, when the fan is activated and air is allowed to flow into the bag, in preferred embodiments the bag is of a weight and texture that permits the fabric to intermittently come into contact with the body to absorb perspiration into the fabric. The fabric is capable of facilitating the wicking of moisture through the fabric to evaporate to the exterior atmosphere of the bag away from the person's body. Exemplary materials that can be used include: woven or non-woven, single or multi-ply, silk, polyester, flannel or cotton, acrylic, nylon, spandex, acrylic microfiber/nylon/spandex, wool, microfleece, nylon parachute silk, non-woven nylon, CoolMax polyester 4-channel fiber, and any CoolMax brand fabric, including EVERYDAY, ACTIVE, EXTREME, UPF, ECO-MADE, EXTRALIFE, FRESH FX, ALL SEASON, and FABRIC FOR WOOL.

Sleep sacks, travel sheets, and sleeping bag liners could also be used as is or modified if needed to cooperate with the fan in embodiments of the system. Representative non-limiting products include: the Sleep Sack by Hammock Bliss #67909; the Equinox Silver Lining sleeping bag liner #41320 (78 in.×36 in., 3.5 oz., compactable to 10.25 in.×7.5 in.×0.75 in.), the Cocoon CoolMax Sleeping Bag liner #690012 (11 oz., 86 in.×33 in., fits in 3.5 in.×7 in. stuff sack), the Sea to Summit Reactor Plus Thermolite Compact Liner #797113 (9.3 oz., polyester, 72 in.×36 in., fits in stuff sack 4 in.×6 in.), the Cocoon CoolMax Travel Sheet #45930 (86 in.×33 in., 10.8 oz.), the Cocoon Cotton TravelSheet Coupler #45920 (86 in.×33 in., 16.9 oz.), the Adaptor CoolMax Travel Liner (9 oz., fits in 3 in.×5 in. stuff sack), and the Cocoon Silk TravelSheet (6.3 oz.) to name a few.

In embodiments of the invention, the material(s) of the bag are stretchy and/or machine washable. Stretchy fabrics will provide a more comfortable sleeping environment as it will feel less restrictive especially to those who may move substantially during sleep. The systems of the invention preferably comprise a bag that is easily detachable and attachable to the fan or other components leading to the fan, such as tubing for directing the flow of the air.

In preferred embodiments, the sleeping bag additionally comprises a layer of silk material on the top of the bag. For example, the silk layer can be sewn along the bottom of the bag (near the person's feet), and along two seams extending lengthwise along the bag to the top of the bag (near the person's head), and along the edge at the top of the bag near the head. In this manner, a second closed compartment is created on the uppermost surface of the sleeping bag. Silk or any other tightly woven material can be used to create this second compartment, so long as the material is semi-impermeable or impermeable to air to allow for the airflow to fill and inflate the second compartment without a substantial amount of air escaping through the outer fabric layer. In this manner, air will flow from the fan directly from the duct or tubing into the upper second closed compartment and not come immediately in contact with the person as it emerges from the duct, which provides for a more comfortable sleeping experience for the person in the bag. Additionally, the top portion of the bag (second compartment) will inflate when the fan turns on which pushes other quilts or blankets off of the person in the bag allowing for air to flow all the way to the person's face as well as allowing for easier evaporation. It is desired to use a fan with sufficient airflow output to keep the upper compartment of the bag inflated while the fan is running.

Inflation of the second compartment of the sleeping bag provides advantages to the cooling systems that other systems do not have. By inflating the second compartment during use, the sleeping bag lifts blankets, duvets, or comforters that are typically in place over the sleeping bag. Lifting of the covers is desired in certain embodiments, where greater circulation of air inside the sleeping compartment is desired, especially around the shoulders and neck of the user. Existing body cooling systems that provide airflow under the bed covers typically are incapable of circulating the air beyond points where the covers contact the bed surface. This is because the airflow from the fan is not powerful enough to lift the covers and if it were the fan would be too loud for a person to continue sleeping with the fan turned on. The inventor has discovered, however, that by containing the air in an air-resistant pocket the pocket will inflate and lift the covers without an increased airflow. In this manner the air can be contained in the upper compartment (or balloon) and allowed to pass through the permeable fabric into the lower compartment where the person is sleeping. This provides sufficient pressure to force the air around the person to locations where it is needed such as the shoulders and neck instead of being trapped under the covers.

As the sleeping bag alone may not provide sufficient coverage and heat insulation for the user during sleep in some seasons, the user of the system may desire to place additional layers of insulation over the sleeping bag, such as a sheet, blanket, and comforter. Ideally, the upper compartment of the sleeping bag is inflated during use to provide lift to covers that weigh approximately 1-2 oz./sq. ft, or to provide lift of a sheet, blanket, and comforter used by the person sleeping.

With the covers lifted up off of the user and the covers providing sufficient counter pressure on the air in the sleeping bag, the air in the upper compartment is forced through the permeable lower fabric layer into the portion of the bag where the user sleeps. Perforations or slits can be made in the material of the lower chamber to allow for a greater flow of air into the lower compartment and/or directed out of the sleeping bag toward the user's neck, head, and shoulders. Preferably, slits or perforations can be incorporated into the main sleeping bag in a manner to provide for the flow of air indirectly from the fan duct system or tubing into the second compartment, then into the first compartment where the person's body is disposed. Care should be taken in using perforations and balancing the number and size of perforations with the goal of keeping the upper chamber inflated, as too many or too large of perforations will decrease the positive pressure situation created by the balloon.

Further, the added air-resistant sheet of material (e.g., the silk layer) can act as a pipeline cover to the fan and offer somewhat better insulating properties if other covers are too cumbersome.

EXAMPLES

Referring now to the figures, specific embodiments of body cooling systems according to the invention are provided. These embodiments are not intended to restrict the invention but rather provide guidance to others in creating systems that accomplish the goals detailed herein. Methods are also included and according to the invention include use of the system embodiments described in this disclosure for cooling a person's body, whether in whole, in part, or in combination with other features.

As shown in the figures and as described below, embodiments can comprise a fan, a sensor, and a control module, and optionally tubing operably connecting the fan and bag at one or more positions on the bag, and a bag for the person to sleep in. As shown in the figures, the fan can be a shrouded fan connected to tubing that splits into two airflow ducts. One of the ducts is connected with the bottom of the bag (near the person's feet in the bag) to deliver air to the interior of the bag. The other duct is disposed near the person's head to deliver air around the head, neck, and shoulders of the person using the bag. In this embodiment, the material of the bag is thin, semi-transparent and stretchy. The airflow being forced into the bag will then circulate around the person, cause the bag to inflate away from the person and/or intermittently contact the person's skin. Excess air can escape the bag through the fabric of the bag, as well as excess moisture in the bag. The temperature sensor will activate the fan control in response to the person's skin temperature or other physiological condition reaching a predetermined level.

Figure 1:
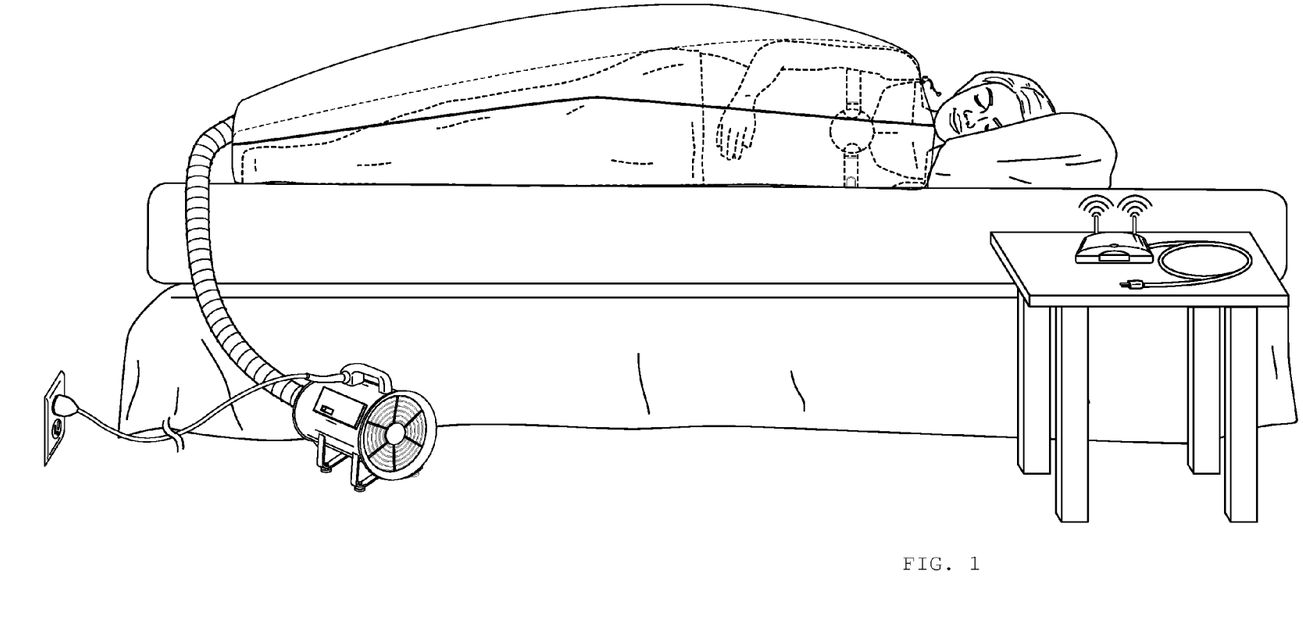
FIG. 1 shows a representative body cooling system according to an embodiment of the invention comprising a single-chamber cooling sack, a fan connected with the cooling chamber by way of a duct, and a wireless control system comprising a sensor, a control module, and a fan module.

FIG. 1 shows a representative body cooling system according to an embodiment of the invention. As shown in FIG. 1, provided is a cooling system comprising: comprising a single-chamber cooling sack, a fan connected with the cooling chamber by way of a duct, and a wireless control system comprising a sensor, a control module, and a fan module.

During operation, a user lies within the single chamber bag typically on a bed and under the usual bed covers, such as a sheet, blanket, and comforter. The remaining components of the system will interact automatically to provide the user with a continuously comfortable environment for sleeping.

The user will wear a sensor for detecting changes in one or more physiological conditions of the user and/or one or more changes in the atmosphere within the bag. The sensor will measure skin or body temperature, skin conductance, relative humidity etc. and will communicate or transmit the information wirelessly to a control module. The information can also be transferred by way of wires, but such a construction may be more uncomfortable for the user.

The desktop control module will receive the data gathered from the sensor and process the data to determine whether a change in the fan settings is needed. The control module can alternatively be disposed on the fan itself, however, if the fan is placed under the bed or in a location where the wireless signal may be obstructed between the modules a stronger wireless device may be needed. The control module can be powered by a wall outlet or power can be provided by another component of the system, such as the fan module. The control module preferably comprises means for charging the sensor battery. The control module is operably connected with a fan module for turning a fan on and off, or for adjusting fan speed.

At the base of the sleeping bag air enters by way of a 4-in. duct operably connected with the fan to deliver an airflow into the sleeping bag. In this embodiment, there is an additional duct disposed along the length of the sleeping bag and along the opening of the bag around the user's head, neck, and shoulders to deliver airflow to the upper portion of the user's body. The ductwork is optional and is preferably constructed of a flexible material so that during use if the user should roll over on the duct, the user will not be injured, made uncomfortable, or awakened.

The control module comprises processing means in order to determine if the information obtained from the sensor is above or below a desired threshold. When the sensor detects a relevant physiological change in the user, the processor instructs and controls the fan module accordingly. For example, if the user's skin temperature raises by 0.5 degrees and the set point of the control module is set to activate the fan at this change, then the control module will turn the fan on to start cooling the user. Advantageously, the set points are programmed at levels that will indicate a hot flash or night sweat is imminent and the fan will be activated to prevent the hot flash from rises to a level that will interfere with the user's sleep.

Figure 2:
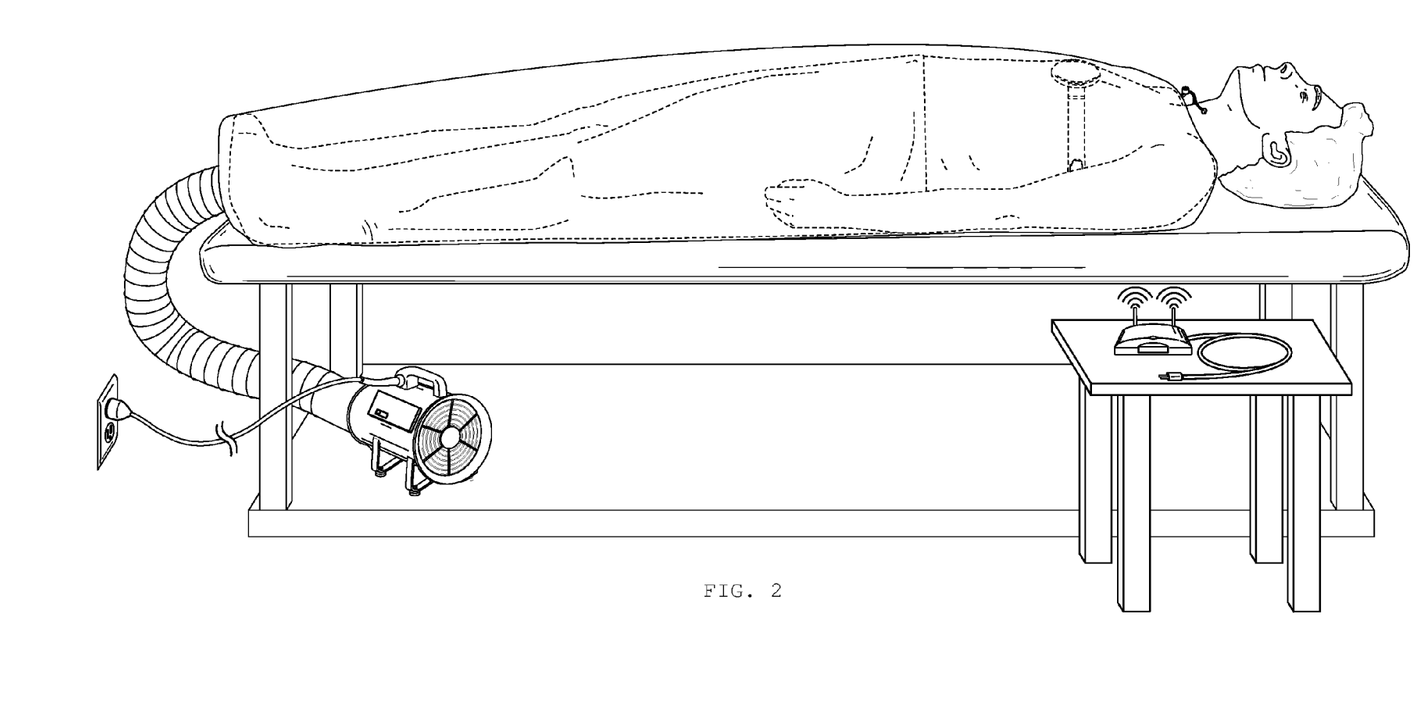
FIG. 2 shows a representative body cooling system of the invention comprising a dual-chamber cooling sack, a fan with duct system, and a wireless control system comprising a sternal sensor, a control module, and a fan module.

FIG. 2 shows a representative body cooling system of the invention comprising a dual-chamber cooling sack, a fan with duct system, and a wireless control system comprising a sternal sensor, a control module, and a fan module. The automated system comprises (i) a sleeping bag made of (a) two fabric sheets joined to form a bag for receiving and covering the body of a user, and (b) an air-resistant sheet of material joined to one of the fabric sheets in a manner to form an upper closed chamber; (ii) a duct in operable communication with the upper closed chamber; (iii) a fan in operable communication with the duct having a speed of 200-400 CFM for inflating the closed chamber and creating a positive airflow from the closed chamber through the fabric sheet into the bag; (iv) a sensor module with one or more sensors for obtaining at least one of a skin temperature, skin relative humidity, or sternal skin conductance measurement; and (v) a control module in operable communication with the sensors for receiving the measurement, comparing the measurement to a set point, and turning the fan on or off in response to the measurement respectively exceeding or falling below the set point.

A user of such an embodiment will lie within the body cooling bag in a first lower chamber of the bag. A second upper chamber of the bag is preferably not accessible to the user but is in operable communication with a fan to deliver airflow to the chamber sufficient to inflate it. Once inflated, the upper chamber elevates the covers up away from the person lying under them to provide for less restricted air flow around the person's body.

The user wears a sensor to detect one or more physical conditions of the user and/or the environment surrounding the user. In this embodiment a chest sensor is shown to measure one or more physiological conditions of the user, such as skin relative humidity. The sensor transmits data to the control module preferably wirelessly. This data is processed by the control module using an algorithm to determine whether the fan should be activated or de-activated. For example, the control module can comprise a threshold level for sternal skin conductance and/or relative humidity. This threshold level will be a point slightly elevated above the user's normal level for sternal skin conductance and relative humidity. Upon detection of these set point(s) being exceeded, the control module will activate the fan. After the fan has been allowed to run for a certain period of time or once a lower threshold is reached, the control module by way of a fan module (or combined control unit) will de-activate the fan.

In preferred embodiments, the fan is in operable communication with only the upper chamber of the sleeping bag to provide two functions. First, the airflow from the fan is used to inflate the upper chamber in a manner to lift any covers laying over the sleeping bag. The pressure created against the upper chamber from the covers then acts to push air from the upper chamber into the lower chamber where the person's body is disposed. Slits or perforations in the material of the lower chamber that is disposed between the two chambers can be used to facilitate the passage of air from the upper to the lower chamber. Generally, the number or size of perforations between the chambers should not be so excessive such that the positive pressure situation created by inflation of the upper chamber is eliminated. Second, the airflow from the fan is introduced to the lower chamber only after passing through the upper chamber and so an indirect airflow from the fan to the user is created. This provides for a more comfortable sleeping experience for the user as the user is not directly exposed to airflow emanating from the fan or ductwork connected or integral to the fan.

The manner of use and operation of the present invention should be apparent from the above description. Accordingly, no further discussion relating to the manner of use and operation will be provided. With respect to the above description then, it is to be realized that the optimum dimensional relationships for the parts of the invention, to include variations in size materials, shape, form, function and manner of operation, assembly and use, are deemed readily apparent and obvious to one skilled in the art, and all equivalent relationships to those illustrated in the drawings and described in the specification are intended to be encompassed by the present invention.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Other embodiments of the invention will be apparent to those skilled in the art from consideration of the specification and practice of the invention. It is intended that the specification and examples be considered as exemplary in nature and that variations that do not depart from the essence of the invention are intended to be within the scope of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

The invention claimed is:

1. An automated system for cooling a body comprising:
   a sleeping bag made of (a) two fabric sheets joined to form a bag for receiving and covering the body of a user, and (b) an air-resistant sheet of material joined to one of the fabric sheets in a manner to form an upper closed chamber;
   wherein the fabric sheets joined to form the bag comprise an absorbent and porous material for reducing moisture and heat in the bag;
   a duct in operable communication with the upper closed chamber;
   a fan in operable communication with the duct having a speed of 200-400 CFM for inflating the closed chamber and creating a positive airflow from the closed chamber through the fabric sheet into the bag;
   a sensor module with one or more sensors for obtaining at least one of a skin temperature, skin relative humidity, or sternal skin conductance measurement; and
   a control module in operable communication with the sensors for receiving the measurement, comparing the measurement to a set point, and turning the fan on or off in response to the measurement respectively exceeding or falling below the set point;
   wherein the control module is programmed to activate the fan in response to the at least one skin temperature, skin relative humidity, or sternal skin conductance measurement being above a set threshold that is below an amount indicative of a hot flash, such that the cooling system is activated prior to the onset of a hot flash; and
   wherein the control module is further programmed to de-activate the fan in response to the at least one skin temperature, skin relative humidity, or sternal skin conductance measurement being below a set threshold.

2. The system of claim 1, wherein the sensor module comprises a skin temperature sensor and a sternal skin conductance sensor.

3. The system of claim 1, wherein the sensor module comprises skin temperature, skin relative humidity, and sternal skin conductance sensors.

4. The system of claim 1, wherein the sensor module comprises a skin relative humidity sensor.

5. The system of claim 1, wherein the sensor and control module communicate wirelessly.

6. The system of claim 1, further comprising a fan module for receiving instructions from the control module for turning on and off the fan.

7. The system of claim 5, wherein the fan module and control module communicate wirelessly.

8. The system of claim 1, wherein during operation the upper closed chamber is inflatable to lift to covers that weigh approximately 1-2 oz./sq. ft.

9. The system of claim 1, wherein the control module is programmed to activate and de-activate the fan in response to the skin relative humidity measurement.

10. An automated system for cooling a body comprising:
    a dual-compartment sleeping bag comprising a first chamber made of (a) two fabric sheets joined to form a bag for receiving and covering the body of a user, and (b) a closed second chamber formed from an air-resistant sheet of material joined to one of the fabric sheets;
    a duct in operable communication with the second chamber;
    a fan in operable communication with the duct having a speed of 200-400 CFM for inflating the second chamber and creating a positive airflow from the second chamber through the fabric sheet into the first chamber;
    a sensor module with one or more sensors for obtaining at least one of a skin temperature, skin relative humidity, or sternal skin conductance measurement; and
    a control module in operable communication with the sensors for receiving the measurement, comparing the measurement to a set point, and turning the fan on or off in response to the measurement respectively exceeding or falling below the set point;
    wherein the control module is programmed to activate the fan in response to the at least one skin temperature, skin relative humidity, or sternal skin conductance measurement being above a set threshold that is below an amount indicative of a hot flash, such that the cooling system is activated prior to the onset of a hot flash; and
    wherein the control module is further programmed to de-activate the fan in response to the at least one skin temperature, skin relative humidity, or sternal skin conductance measurement being below a set threshold.

11. The system of claim 10, wherein the fabric sheets joined to form the bag comprise an absorbent and porous material for reducing moisture and heat in the bag.

12. The system of claim 10, wherein the sensor module comprises a skin temperature sensor and a sternal skin conductance sensor.

13. The system of claim 10, wherein the sensor module comprises skin temperature, skin relative humidity, and sternal skin conductance sensors.

14. The system of claim 10, wherein the sensor module comprises a skin relative humidity sensor.

15. The system of claim 10, wherein the control module is programmed to activate and de-activate the fan in response to the skin relative humidity measurement.

* * * * *